United States Patent [19]

Corkins et al.

[11] 4,264,533

[45] Apr. 28, 1981

[54] PREPARATION OF S-CHLOROMETHYLATED O-ALKYL SUBSTITUTED PHOSPHODITHIOIC ACIDS

[75] Inventors: H. Glenn Corkins, Mentor; Louis Storace, Mentor-on-the-Lake; William W. Brand, Painesville, all of Ohio

[73] Assignee: Diamond Shamrock Corporation, Dallas, Tex.

[21] Appl. No.: 100,102

[22] Filed: Dec. 4, 1979

[51] Int. Cl.$^3$ .............................................. C07F 9/165
[52] U.S. Cl. .................................... 260/986; 260/963
[58] Field of Search .......................................... 260/986

[56] References Cited

U.S. PATENT DOCUMENTS

| | | | |
|---|---|---|---|
| 2,092,712 | 9/1937 | Clifford | 260/44 |
| 3,020,304 | 2/1962 | Scherer et al. | 260/963 |
| 3,052,709 | 9/1962 | Strube et al. | 260/986 |
| 3,669,981 | 6/1972 | Pera | 260/306 |
| 3,896,219 | 7/1975 | Pianka | 424/225 |

OTHER PUBLICATIONS

Sexton et al. "J. of Chem. Soc.", (London), (1948) p. 1717.
Dolman et al. "Rec. des Travaux Chem. des Pays-Bas", vol. 88 (1969), pp. 417–424.

*Primary Examiner*—Anton H. Sutto
*Attorney, Agent, or Firm*—Arthur S. Collins

[57] ABSTRACT

A novel and efficient method for preparing S-chloromethyl derivatives of O-alkylphosphorodithioic acids involves reacting the S-hydroxymethyl derivative of such an acid under substantially anhydrous conditions with a suitable acid chloride in a chemically unreactive organic liquid which is a solvent for both said S-hydroxymethyl derivative and said acid chloride. Suitable acid chlorides are $PCl_5$, $PCl_3$, acetyl chloride, chlorinated derivatives of acetyl chloride, oxalyl chloride, phosgene, thionyl chloride, sulfuryl chloride, aryl sulfonyl chlorides and chloro- or nitro-substituted aryl sulfonyl chlorides.

15 Claims, No Drawings

PREPARATION OF S-CHLOROMETHYLATED O-ALKYL SUBSTITUTED PHOSPHODITHIOIC ACIDS

INTRODUCTION

This invention is concerned with methods for preparing S-chloromethyl derivatives of O-alkyl substituted phosphodithioic acids such as O,O-dialkyl phosphorodithioic acids and O-alkyl, alkyl phosphonodithioic acids. Said derivatives are of interest as functional intermediates in organic syntheses and are of industrial importance in their own right in view of their biological activity and utility as pesticides and the like.

BACKGROUND OF THE INVENTION

In the art of preparing S-chloromethyl derivatives of O-alkyl substituted phosphodithioic acids, the accepted practice has involved reacting a suitable salt of such an acid with bromochloromethane under conditions favoring conversion of the salt forming moiety to a bromide salt, as illustrated by U.S. Pat. Nos. 3,020,304 (Scherer et al.) and 3,896,219 (Pianka). A related process incorporating particular, specialized conditions under which a more readily available reactant, namely dichloromethane, can be used effectively as the S-chloromethylating agent forms the subject of copending U.S. Application Ser. No. 053,066 filed on June 28, 1979, by W. W. Brand and having a common assignee with the present application.

The present invention is directed to entirely different methods for preparing S-chloromethyl derivatives of O-alkyl substituted phosphodithioic acids involving the reactions of their S-hydroxymethyl analogs with suitable acid chlorides. The choice of suitable acid chloride reactants is rather wide and includes such common inorganic species as phosphorus pentachloride and phosphorus trichloride. Indeed, due to the ready availability and high reactivity of the acid chloride reagents employed, the novel process of the present invention provides several important advantages in the manufacture of the desired derivatives. For example, lower temperature operations are rendered more practical, including efficient conversions at ordinary room temperatures (or even below). In fact, in many cases, the selectivity of the reaction with regard to yield of the desired derivative is close to optimum at ordinary room temperatures. Accordingly, the subject processes are very energy efficient and economical to operate, especially since a large excess of main reactant is not needed and product recovery is straight forward.

SUMMARY OF THE INVENTION

We have discovered that S-chloromethyl derivatives of O-alkyl substituted phosphodithioic acids can be prepared in excellent yields from their S-hydroxymethyl analogs by reacting the latter with certain acid chlorides as specified hereinafter under essentially anhydrous conditions in a suitable unreactive organic solvent. The effective acid chlorides are as follows: phosphorus pentachloride, phosphorus trichloride, phosgene, thionyl chloride, sulfuryl chloride, oxalyl chloride, acetyl chloride, chloro-substituted acetyl chlorides, aryl sulfonyl chlorides and chloro- and nitro-substituted aryl sulfonyl chlorides. Generally, ordinary pressures and mild temperatures are satisfactory for use in conducting the desired reaction, but the addition of dry HCL and/or a Lewis Acid catalyst such as $ZnCl_2$ or $SnCl_4$ can serve to expedite the desired reaction, and the use thereof is an important practical option for the present invention, especially when any of the acid chloride compounds other than $PCL_5$ is employed.

DETAILED DESCRIPTION OF THE PREFERRED EMBODIMENTS

The S-chloromethylated derivatives of primary interest herein are those of O,O-dialkyl phosphorodithioic acids and particularly of such acids wherein each alkyl group is a lower alkyl, e.g., one containing from 1 to about 6 carbon atoms. Accordingly, the preferred starting materials for the present invention are S-(hydroxymethyl) derivatives of such phosphorodithioic acids, having the general structure:

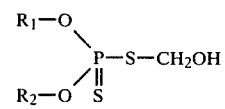

wherein each of $R_1$ and $R_2$ is a lower alkyl group, preferably of 1 to 6 carbon atoms. For example, O,O-diethyl-S-(hydroxymethyl)phosphorodithioate is a most preferred individual compound having said general structure.

If not otherwise available, the starting S-hydroxymethyl derivatives can be prepared by reacting the appropriate O-alkyl substituted phosphorodithioic acid with formaldehyde in the presence of anhydrous hydrogen chloride. Said reaction is advantageously conducted in anhydrous diethyl ether or other suitable dry organic solvent at moderate to low temperatures using a convenient form of formaldehyde, such a paraformaldehyde or s-trioxane. For best results in promoting good yields and purity of the desired S-hydroxymethyl derivatives, the reaction temperature should be between about 0° and about 100° C. and preferably at about room temperature or below.

Hydrocarbons and chlorinated hydrocarbons are preferred for use as the organic solvent in which the reaction between said S-(hydroxymethyl) derivatives, and the acid chloride is carried out in accordance with the present invention. Ethers can also be used satisfactorily except for the methyl and cyclic ethers, which are too reactive toward some acid chlorides. Because of their ready availability and favorable price, many of the simpler molecular species of these respective classes of organic liquids are ideal for use as the liquid solvent medium herein, including hexane, heptane, benzene, toluene, carbon tetrachloride, methylene chloride, chlorobenzene, diethyl ether and the like. Moreover, such liquids also tend to have adequate solvent power for such optional promoters and catalysts as HCl and $ZnCl_2$ so as to assure their effectiveness whenever such use is desirable.

In most cases, suitable reaction temperatures for practicing the present invention can range from around 0° to about 120° C. Somewhat higher reaction temperatures are often feasible but are generally unnecessary and sometimes even disadvantageous due to increased promotion of a competing side reaction and resultant loss of yield or purity of the desired end product. In fact, in the case of phosphorus pentachloride, the subject process proceeds at adequate speeds at temperatures as low as 0° C. or less.

If desired, the processes of this invention can be operated under liquid reflux conditions as is often done in reaction systems utilizing a solvent medium. However, it is preferred in most of the present reaction systems to operate at lower than active refluxing temperatures, especially when an acid chloride compound other than PCl$_5$ is involved.

The subject invention is entirely amenable to being practiced at or near normal pressures with excellent results. Accordingly, the only time that the use of substantially higher than normal pressures would be of major benefit would be when a normally gaseous material like phosgene comprises one of the principal reactants in the subject process.

From the point of view of both efficiency and convenience, the temperature range of primary interest is between about 20° and about 100° C. considering all the various acid chloride species generally, with the range from about 25° to about 75° C. being preferred in most cases. However, the rates of reaction with PCl$_3$ and the other acid chloride compounds are generally considerably slower than those with PCl$_5$ under a given set of conditions. Accordingly, PCl$_5$ is normally the preferred acid chloride in the present invention, and attractive yields of the desired chloromethyl derivatives can generally be obtained therewith using a satisfactory inert liquid solvent in very reasonable reaction times of only about 1 to about 4 hours, especially at room temperatures or above (even without added promoters or catalysts).

The reaction of the PCl$_5$ with an O,O-dialkyl-S-(hydroxymethyl)phosphorodithioate produces the desired S-chloromethyl derivative along with POCl$_3$ and HCl in accordance with the chemical equation:

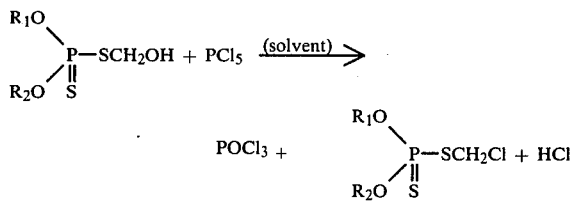

Close to equimolar amounts of PCl$_5$ and the starting hydroxymethyl compound are therefore indicated, and such ratios enable excellent yields to be attained. The purity of the end product appears to be optimized when the reaction is conducted below about 75° C. using a slight excess (e.g., about 10 percent) of PCl$_5$.

The next most preferred acid chloride compound in the present invention is PCl$_3$ because it too can produce good yields of the desired chloromethyl compounds under proper conditions, although longer reaction times are inherently needed for optimum results (e.g., about 8 to 30 hours). Thus, some special stimulus is generally required to achieve a practical production process using PCl$_3$, such as either or both of the following: (1) the use of somewhat elevated temperatures (i.e., above normal room temperatures) together with either the addition of supplemental hydrogen chloride and/or the use of a closed system to insure effective promotion of the reaction by means of the by-product HCl initially generated in situ; (2) the delayed addition of at least a catalytic amount of a Lewis acid compound (e.g., ZnCl$_2$).

The overall reaction of PCl$_3$ with an O,O-dialkyl-S-(hydroxymethyl)phosphorodithioate can be represented by the following net equation:

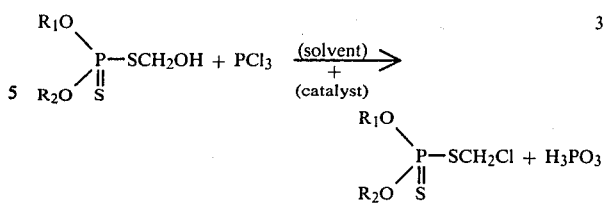

Evidence strongly indicates that a step-wise reaction is actually involved wherein by-product HCl ad phosphite ester linkages between the phosphorous in PCl$_3$ and the S-(hydroxymethyl) groups in the starting organic compound are formed first with the resultant phosphite ester structure subsequently being displaced by a chloride group to yield the desired S-chloromethyl derivative. Both the early and final stages of this complex step-wise reaction respond favorably to moderately elevated temperatures and the promoting effect of hydrogen chloride, so that a closed system and/or the addition of supplemental hydrogen chloride can advantageously be used from the start of the reaction between PCl$_3$ and the S-(hydroxymethyl) compound. However, in order to insure beneficial effect on the course of the reaction with PCl$_3$ through use of a strong catalyst like ZnCl$_2$, it is generally necessary to delay the addition of same for a significant period of time, usually at least an hour, and preferably more. Evidently, said catalysts are not very effective in promoting the initial phase of the PCl$_3$ reaction and prone to be tied up by a direct reaction involving the starting S-hydroxymethyl compound and leading to the dehydration (or self-condensation) of some of same to form the symmetrical bis(O,O-dialkyl-dithiophosphoromethyl) ether as represented by the following equation:

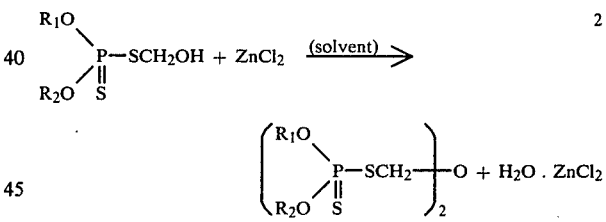

One advantage of using PCl$_3$ as the acid chloride reagent herein is that one mole of PCl$_3$ is capable of reacting with 3 moles of the starting S-hydroxymethyl compound. In actual practice, we have used as little as 0.33 moles of PCl$_3$ per mole of starting organic compound and still converted 60 to 70 percent of the latter to the desired S-chloromethyl derivative in overall reaction times of about 1 day at room temperature with careful promotion of reaction in a good solvent by means of HCl and/or delayed addition of catalytic amounts of ZnCl$_2$. The preferred molar ratio of PCl$_3$ to starting hydroxymethyl compound is between about 0.3 and about 1.2 as respectable yields can generally be attained therewith in reasonable overall reaction times of about 8 to 24 hours. Even larger excesses of PCl$_3$ up to molar ratios of as much as 3:1 to 4:1 are also satisfactory, but do not seem to offer a commensurate gain in either reaction speed, or yield of the desired end product, at least when operating within the normally favored temperature range of from about 20° to about 100° C.

The remaining classes of acid chlorides are also considerably slower in reactivity than PCl$_5$. Therefore, in almost all cases, it is advantageous to use promoters (e.g., HCl) and/or catalysts to expedite the reaction of these additional species. Moreover, it is generally advisable to operate at somewhat elevated temperatures when using these additional species unless ZnCl$_2$ or equivalent catalytic species are employed in more than merely catalytic amounts. Delayed addition of at least some of the ZnCl$_2$ (or its equivalents) is sometimes desirable here, too, especially when more than catalytic amounts thereof are involved. However, this precaution is not nearly as important in regard to obtaining high product yields as in the case of the PCl$_3$ reaction discussed previously.

The reactions involving such additional classes of acid chloride compounds most likely also involve a step-wise sequence somewhat analogous to that in the PCl$_3$ case.

Taking acetyl chloride as the representative species of said classes, the following chemical equation illustrates a logical two-step sequence:

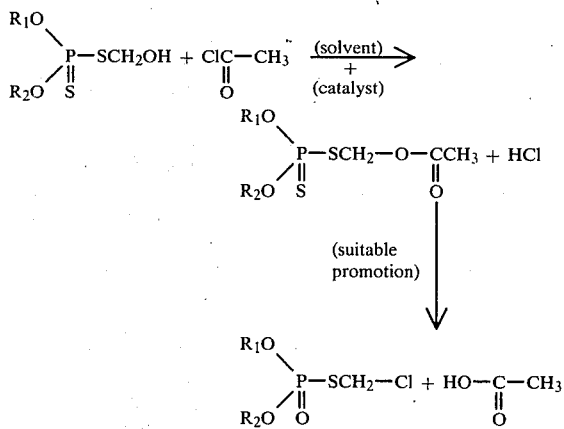

Even though bifunctional acid chlorides (like oxalyl chloride) are included among these alternative species, they are not actually capable of reacting with substantially more than about equimolar amounts of the starting S-hydroxymethyl compound. In fact, in order to obtain respectable overall yields of the order of 50 percent or more of the desired chloromethyl derivatives, it is usually necessary to use at least equimolar amounts of said acid chlorides as well as the special promotion measures already described hereinabove. Furthermore, elevated temperatures and/or more than catalytic amounts of ZnCl$_2$ or the like are usually needed to assure good conversions within the reaction times generally desired for practical production processes.

In working up the final reaction mixtures of this invention for product recovery, most of the major by-products such as HCl, POCl$_3$, H$_3$PO$_3$, aryl sulfonic acids, acetic acid and the like are easily washed out or extracted from the organic liquid solution using water or alkaline aqueous solutions containing sodium bicarbonate or the like. Provided a good conversion of the starting S-hydroxymethyl compound to the desired chloromethyl derivative has been accomplished, products of satisfactory purity for many purposes can often be obtained simply by suitable evaporation of the solvent along with the relatively volatile impurities which were not already removed by the aqueous washing step. Additional purification of the products can be achieved by careful vacuum distillation techniques as is well known in the art.

A better understanding of the operational details and other practical aspects of this invention may be obtained by a study of the following specific experimental examples, in which the amounts of various materials specified therein are given in parts by weight unless otherwise indicated.

EXAMPLE A

Preparation of S-hydroxymethyl Derivative of O,O-dialkyl Phosphorodithioic Acid

Forty-five grams of purified O,O-diethylphosphorodithioic acid was dissolved in about 500 ml of diethyl ether. After adding 7.3 grams of paraformaldehyde, the mixture was cooled to about 0° C. Said mixture was the stirred for about 2.5 hours while bubbling anhydrous hydrogen chloride through same continuously. The diethyl ether solvent was removed by rotary evaporation leaving 52 grams of a yellow oil.

The nuclear magnetic resonance spectrum of a sample of this oil dissolved in deuterated chloroform, using tetramethylsilane as an internal standard, indicated that the desired S-(hydroxymethyl) derivative comprised about 98 mole percent of said oil with the balance being largely the bis(O,O-diethyldithiophosphoromethyl)ether. These structures were also confirmed by infrared studies. Furthermore, the presence in said oil of the corresponding S-chloromethyl derivative was not detectable by either analytical technique.

The commercial grade of O,O-diethylphosphorodithioic acid (about 90 percent pure, by weight) was also used to synthesize the S-(hydroxymethyl) derivative in accordance with this same procedure. The S-(hydroxymethyl) product obtained assayed close to 90 percent purity, by weight. Such a product was the starting material in most of the following working examples.

EXAMPLE 1

To a stirring solution of 0.94 grams of approximately 90 percent pure O,O-diethyl-S-(hydroxymethyl)phosphorodithioate in 100 ml of dry carbon tetrachloride was added 1.08 grams of solid PCl$_5$. Stirring was continued at room temperature for about 4 hours. Then the reaction mixture was poured into about 25 ml of water. After separating, the organic layer was washed with a saturated aqueous solution of sodium bicarbonate. The organic layer was then dried over anhydrous sodium sulfate and the carbon tetrachloride solvent removed by rotary evaporation to leave about 1 gram of yellow oil. The concentration of S-chloromethyl-O,O-diethylphosphorodithioate in this oil was determined to be about 79 percent, by weight, by means of quantitative NMR analysis using the external standard method of comparison. This represented a yield of S-chloromethyl-O,O-diethylphosphorodithioate of 86 percent.

EXAMPLES 2–4

Using the procedure of Example 1, 3 similar reactions were carried out using the same materials and conditions except that other dry, inert solvents were substituted for the carbon tetrachloride. The solvents used and the yields of S-chloromethyl-O,O-diethylphosphorodithioate realized are summarized in the following table:

TABLE 1

Reactions of S-hydroxymethyl analog with PCl$_5$ at R. T.

| Example No. | Solvent Used | Yield of S-chloromethyl Derivative (by wt.) |
|---|---|---|
| 2 | Hexane | 79% |
| 3 | Toluene | 77% |
| 4 | Diethyl Ether | 62% |

However, when it was attempted to use solvents like tetrahydrofuran and 1,2-dimethoxyethane as the reaction medium in the above-described procedures, the maximum yields of S-chloromethyl-O,O-diethylphosphorodithioate realized were quite low (far less than 50 percent) die to interfering reactions by said solvent with phosphorus pentachloride.

EXAMPLE 5

Heptane (70 ml) was heated to reflux (98° C.) and 1.06 grams of PCl$_5$ added, following by 0.92 gram of O,O-diethyl-S-hydroxymethylphosphorodithioate (96 percent, by weight, purity). The mixture was stirred for about 1 hour while maintaining solvent reflux conditions, then cooled in ice bath to about 20° C. and diluted to 100 cc total volume with additional heptane. Using gas chromatography analysis (external standard method), the concentration of S-choromethyl-O,O-diethylphosphorodithioate was determined to be 0.0035 molar, representing a yield of about 86 percent of theoretical.

Additional reactions were carried out at lower temperatures using the same quantities of reactants and 100 ml of heptane as the solvent reaction medium. The reaction temperatures, times and resultant yield of the S-chloromethyl derivative in these reactions are indicated in Table 2.

TABLE 2

Reactions with PCl$_5$ in Heptane

| Reaction Temp. | Reaction Time | Approx. Yield (by Gas Chromatography) |
|---|---|---|
| 22° C. | 4 hours | 88% |
| 0° C. | 4 hours | 60% |
| −35° C. | 18 hours | 21% |

EXAMPLE 6

To a stirring solution of 5.4 grams of 90 percent pure O,O-diethyl-S-(hydroxymethyl)phosphorodithioate in 150 ml of anhydrous diethyl ether was added 1.3 grams of PCl$_3$ (representing a mole ratio of PCl$_3$/S-hydroxymethyl analog of about 0.4). Stirring was continued while sparging anhydrous hydrogen chloride continuously through the reaction mixture at room temperature for 18 hours. An analysis of the resulting ether solution at this point by NMR (external standard method) indicated that about 51 percent of the original O,O-diethyl-S-(hydroxymethyl)phosphorodithioate had been converted to the desired S-chloromethyl derivative. The total yield of the desired product reached slightly over 60 percent when the reaction was allowed to continue for about 36 hours.

When the same reaction was conducted with the exception that the proportion of PCl$_3$ was increased to about equimolar and anhydrous ZnCl$_2$ catalyst was included in a concentration of about 1 percent, by weight, of the starting S-hydroxymethyl analog, a 60 percent conversion to the desired S-chloromethyl derivative was achieved in about 18 hours. This conversion level was further increased to about 70 to 80 percent when substantially the same reaction was run except that a much larger addition of anhydrous ZnCl$_2$ was made on a delayed basis (e.g., approximately an equimolar amount at the end of about 4 hours).

Furthermore, substantially the same conversion levels and yields reported above are realized in considerably shorter reaction times when the above experiments are run at somewhat elevated temperatures (e.g., about 50 percent reductions in time can be realized at temperatures of about 50° to 60° C.).

EXAMPLES 7–9

These examples correspond closely to Example 6 except that the anhydrous inert solvent used was carbon tetrachloride, heptane, and toluene, respectively, instead of diethyl ether. No problems or appreciable changes in results were encountered with any of same.

EXAMPLE 10

To a stirring solution of 0.5 gram of 90 percent pure O,O-diethyl-S-(hydroxymethyl)phosphorodithioate in 50 ml of anhydrous diethyl ether, was added 0.5 gram of acetyl chloride (representing a mole ratio of acetyl chloride to S-hydroxymethyl compound of about 3). Approximately 1 gram of anhydrous ZnCl$_2$ (again about 3:1 molar ratio relative to the S-hydroxymethyl compound) was also added, and anhydrous hydrogen chloride was continuously sparged through the reaction mixture at room temperature for about 6 hours.

At this point, a sample analyzed by NMR showed the presence of significant amounts of S-(acetoxymethyl)-O,O-diethylphosphorodithioate in the reaction mixture but very little of the S-chloromethyl derivative ultimately desired. However, after standing for about 4 days in a closed flask at room temperature, the reaction mixture was worked up for product recovery. After washing with water, a saturated aqueous solution of sodium bicarbonate, and a saturated aqueous solution of sodium chloride in sequence, the isolated ether layer was dried over sodium sulfate and then subjected to rotary evaporation to yield 0.37 gram of yellow oil. This oil, analyzed by quantitative NMR (external standard method) assayed about 55 percent, by weight, S-(chloromethyl)-O,O-diethylphosphorodithioate representing a yield of about 42 percent.

The above detailed examples have been provided as illustrative embodiments of the present invention and the results obtainable in the practice of same. As such, many substitutions and other changes can be made therein as will be obvious from the overall teachings we have presented regarding the scope of our invention. For example, other O,O-dialkyl derivatives can be used in place of the O,O-diethyl compounds, other acid chlorides can be substituted for the model species exemplified, and/or other Lewis acid compounds such as tin chloride can serve as catalysts instead of ZnCl$_2$. Accordingly, the appended claims are directed to the full scope of our invention including all variations thereof which are obvious to those skilled in the art.

What is claimed is:

1. Process for preparing S-chloromethylated derivatives of O-alkyl phosphorodithioic acids which comprises reacting an S-hydroxymethyl derivative of such an acid under substantially anhydrous conditions with an acid chloride chosen from the group consisting of PCl$_5$, PCl$_3$, acetyl chloride, chlorinated derivatives of acetyl chloride, oxalyl chloride, phosgene, thionyl chloride, sulfuryl chloride, aryl sulfonyl chlorides and chloro- or nitro-substituted aryl sulfonyl chlorides in a chemically unreactive organic liquid which is a solvent for both said S-hydroxymethyl derivative and said acid chloride under the reaction conditions employed and, at least when PCl₅ is not used, promoting said reaction by maintaining a ready supply of free hydrogen chloride in said organic liquid.

2. A process as in claim 1 wherein the mol ratio of acid chloride to said S-hydroxymethyl derivative is between about 0.3 and about 4.0.

3. A process as in claim 2 wherein said mol ratio is between about 0.5 and about 1.5.

4. A process as in claim 1 wherein the temperature is not substantially less than 0° C. and not substantially more than 120° C.

5. A process as in claim 4 wherein the temperature is between about 20° and about 100° C.

6. A process as in claim 4 wherein the temperature is between about 25° and about 75° C.

7. A process as in claim 1 wherein the reaction is stimulated by increasing the supply of hydrogen chloride, adding an acidic catalyst, or both.

8. A process as in claim 7 wherein a Lewis acid compound is the acidic catalyst.

9. A process as in claim 8 wherein ZnCl₂ is used as the Lewis acid compound.

10. A process as in claim 9 wherein ZnCl₂ is employed in more than catalytic amounts.

11. A process as in claim 10 wherein at least the major portion of said ZnCl₂ is added after a major portion of said S-hydroxymethyl derivative has reacted.

12. A process as in claim 1 wherein said organic liquid is chosen from the group consisting of hydrocarbons, carbon tetrachloride, other chlorinated hydrocarbons, and ethers other than methyl or cyclic ethers.

13. A process as in claim 1 wherein said S-hydroxymethyl derivatives are characterized by the general structure:

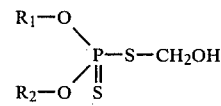

wherein each of R₁ and R₂ is a lower alkyl group.

14. A process as in claim 13 wherein said acid chloride is PCl₅ or PCl₃.

15. A process as in claim 14 wherein said acid chloride is PCl₅.

* * * * *